(12) United States Patent
Dunki-Jacobs (10) Patent No.: US 7,713,265 B2
(45) Date of Patent: May 11, 2010

(54) APPARATUS AND METHOD FOR MEDICALLY TREATING A TATTOO

(75) Inventor: Robert J. Dunki-Jacobs, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 298 days.

(21) Appl. No.: 11/615,140

(22) Filed: Dec. 22, 2006

(65) Prior Publication Data

US 2008/0154248 A1 Jun. 26, 2008

(51) Int. Cl.
*A61B 18/18* (2006.01)

(52) U.S. Cl. ................. 606/10; 606/9; 606/12; 607/88; 128/898

(58) Field of Classification Search .............. 606/8–12; 607/88–92; 128/898
See application file for complete search history.

(56) References Cited

U.S. PATENT DOCUMENTS

| | | | |
|---|---|---|---|
| 3,758,199 A | 9/1973 | Thaxter |
| 3,959,582 A | 5/1976 | Law et al. |
| 4,082,635 A | 4/1978 | Fritz et al. |
| 4,141,362 A | 2/1979 | Wurster |
| 4,313,431 A | 2/1982 | Frank |
| 4,379,039 A | 4/1983 | Fujimoto et al. |
| 4,403,273 A | 9/1983 | Nishioka |
| 4,409,477 A | 10/1983 | Carl |
| 4,421,382 A | 12/1983 | Doi et al. |
| 4,524,761 A | 6/1985 | Hattori et al. |
| 4,527,552 A | 7/1985 | Hattori |
| 4,573,465 A | 3/1986 | Sugiyama et al. |
| 4,576,999 A | 3/1986 | Eckberg |
| 4,597,380 A | 7/1986 | Raif et al. |
| 4,643,967 A | 2/1987 | Bryant |

(Continued)

FOREIGN PATENT DOCUMENTS

DE 3837248 5/1990

(Continued)

OTHER PUBLICATIONS

Ra, H. et al., "Biomedical Optics & Medical Imaging—Microtechnology enables endoscopic confocal microscopy," SPIE (http://spie.org) (2007).

(Continued)

*Primary Examiner*—Ahmed M Farah
(74) *Attorney, Agent, or Firm*—Victor C. Moreno (57) ABSTRACT

Apparatus for medically treating a tattoo includes a scanned light beam unit having a light beam source assembly adapted to emit light pulses at different wavelengths, a scanner, light detector(s), and a controller operatively connected to the light beam source assembly and the scanner. The controller is adapted: to control the scanned light beam unit to illuminate a first light-pulse-sized region of the tattoo using the light beam source assembly at different wavelengths and at relatively low power; to use the light detector(s) to detect a least-reflecting wavelength of the illumination of the first light-pulse-sized region of the tattoo; and to control the scanned light beam unit to medically treat the first light-pulse-sized region of the tattoo using the light beam source assembly at a wavelength substantially equal to the least-reflecting wavelength and at relatively high power. A method is disclosed for medically treating a tattoo which uses the apparatus.

20 Claims, 3 Drawing Sheets

U.S. PATENT DOCUMENTS

| | | | |
|---|---|---|---|
| 4,676,231 A | 6/1987 | Hisazumi et al. |
| 4,760,840 A | 8/1988 | Fournier, Jr. et al. |
| 4,803,550 A | 2/1989 | Yabe et al. |
| 4,872,458 A | 10/1989 | Kanehira et al. |
| 4,902,083 A | 2/1990 | Wells |
| 4,902,115 A | 2/1990 | Takahashi |
| 4,934,773 A | 6/1990 | Becker |
| 4,938,205 A | 7/1990 | Nudelman |
| 5,003,300 A | 3/1991 | Wells |
| 5,023,905 A | 6/1991 | Wells et al. |
| 5,048,077 A | 9/1991 | Wells et al. |
| 5,074,860 A | 12/1991 | Gregory et al. |
| 5,078,150 A | 1/1992 | Hara et al. |
| 5,163,936 A | 11/1992 | Black et al. |
| 5,163,945 A | 11/1992 | Ortiz et al. |
| 5,172,685 A | 12/1992 | Nudelman |
| 5,188,633 A * | 2/1993 | Kratzer et al. .............. 606/12 |
| 5,192,288 A | 3/1993 | Thompson et al. |
| 5,200,819 A | 4/1993 | Nudelman et al. |
| 5,200,838 A | 4/1993 | Nudelman et al. |
| 5,207,670 A * | 5/1993 | Sinofsky ................ 606/8 |
| 5,218,195 A | 6/1993 | Hakamata |
| 5,251,025 A | 10/1993 | Cooper et al. |
| 5,251,613 A | 10/1993 | Adair |
| 5,269,289 A | 12/1993 | Takehana et al. |
| 5,318,024 A | 6/1994 | Kittrell et al. |
| 5,334,991 A | 8/1994 | Wells et al. |
| 5,368,015 A | 11/1994 | Wilk |
| 5,370,643 A | 12/1994 | Krivoshlykov et al. |
| 5,387,197 A | 2/1995 | Smith et al. |
| 5,393,647 A | 2/1995 | Neukermans et al. |
| 5,436,655 A | 7/1995 | Hiyama et al. |
| 5,467,104 A | 11/1995 | Furness, III et al. |
| 5,488,862 A | 2/1996 | Neukermans et al. |
| 5,531,740 A * | 7/1996 | Black ............... 606/9 |
| 5,545,211 A | 8/1996 | An et al. |
| 5,552,452 A | 9/1996 | Khadem et al. |
| 5,557,444 A | 9/1996 | Melville et al. |
| 5,590,660 A | 1/1997 | MacAulay et al. |
| 5,596,339 A | 1/1997 | Furness, III et al. |
| 5,608,451 A | 3/1997 | Konno et al. |
| 5,629,790 A | 5/1997 | Neukermans et al. |
| 5,648,618 A | 7/1997 | Neukermans et al. |
| 5,649,952 A | 7/1997 | Lam |
| 5,657,165 A | 8/1997 | Karpman et al. |
| 5,658,710 A | 8/1997 | Neukermans |
| 5,659,327 A | 8/1997 | Furness, III et al. |
| 5,694,237 A | 12/1997 | Melville |
| 5,701,132 A | 12/1997 | Kollin et al. |
| 5,713,891 A | 2/1998 | Poppas |
| 5,728,121 A | 3/1998 | Bimbo et al. |
| 5,735,792 A | 4/1998 | Vanden Hoek et al. |
| 5,742,419 A | 4/1998 | Dickensheets et al. |
| 5,742,421 A | 4/1998 | Wells et al. |
| 5,751,465 A | 5/1998 | Melville et al. |
| 5,768,461 A | 6/1998 | Svetkoff et al. |
| 5,797,944 A | 8/1998 | Nobles et al. |
| 5,817,061 A | 10/1998 | Goodwin et al. |
| 5,823,943 A | 10/1998 | Tomioka et al. |
| 5,827,176 A | 10/1998 | Tanaka et al. |
| 5,827,190 A | 10/1998 | Palcic et al. |
| 5,841,553 A | 11/1998 | Neukermans |
| 5,861,549 A | 1/1999 | Neukermans et al. |
| 5,867,297 A | 2/1999 | Kiang et al. |
| 5,895,866 A | 4/1999 | Neukermans et al. |
| 5,903,397 A | 5/1999 | Melville et al. |
| 5,907,425 A | 5/1999 | Dickensheets et al. |
| 5,913,591 A | 6/1999 | Melville |
| 5,947,930 A | 9/1999 | Schwemberger et al. |
| 5,969,465 A | 10/1999 | Neukermans et al. |
| 5,969,871 A | 10/1999 | Tidwell et al. |
| 5,982,528 A | 11/1999 | Melville |
| 5,982,555 A | 11/1999 | Melville et al. |
| 5,993,037 A | 11/1999 | Tomioka et al. |
| 5,995,264 A | 11/1999 | Melville |
| 6,007,208 A | 12/1999 | Dickensheets et al. |
| 6,008,781 A | 12/1999 | Furness, III et al. |
| 6,013,025 A | 1/2000 | Bonne et al. |
| 6,016,440 A | 1/2000 | Simon et al. |
| 6,017,356 A | 1/2000 | Frederick et al. |
| 6,017,603 A | 1/2000 | Tokuda et al. |
| 6,024,744 A | 2/2000 | Kese et al. |
| 6,043,799 A | 3/2000 | Tidwell |
| 6,044,705 A | 4/2000 | Neukermans et al. |
| 6,046,720 A | 4/2000 | Melville et al. |
| 6,049,407 A | 4/2000 | Melville |
| 6,056,721 A | 5/2000 | Shulze |
| 6,057,952 A | 5/2000 | Kubo et al. |
| 6,059,720 A | 5/2000 | Furusawa et al. |
| 6,061,163 A | 5/2000 | Melville |
| 6,064,779 A | 5/2000 | Neukermans et al. |
| 6,069,725 A | 5/2000 | Melville |
| 6,086,528 A | 7/2000 | Adair |
| 6,086,531 A | 7/2000 | Tomioka et al. |
| 6,088,145 A | 7/2000 | Dickensheets et al. |
| 6,097,353 A | 8/2000 | Melville et al. |
| 6,122,394 A | 9/2000 | Neukermans et al. |
| 6,139,175 A | 10/2000 | Tomioka et al. |
| 6,140,979 A | 10/2000 | Gerhard et al. |
| 6,151,167 A | 11/2000 | Melville |
| 6,154,305 A | 11/2000 | Dickensheets et al. |
| 6,154,321 A | 11/2000 | Melville et al. |
| 6,157,352 A | 12/2000 | Kollin et al. |
| 6,166,841 A | 12/2000 | Melville |
| 6,172,789 B1 | 1/2001 | Kino et al. |
| 6,178,346 B1 | 1/2001 | Amundson et al. |
| 6,179,776 B1 | 1/2001 | Adams et al. |
| 6,191,761 B1 | 2/2001 | Melville et al. |
| 6,192,267 B1 | 2/2001 | Scherninski et al. |
| 6,200,595 B1 | 3/2001 | Motoyashiki et al. |
| 6,204,829 B1 | 3/2001 | Tidwell |
| 6,204,832 B1 | 3/2001 | Melville et al. |
| 6,207,392 B1 | 3/2001 | Weiss et al. |
| 6,210,401 B1 * | 4/2001 | Lai ..................... 606/12 |
| 6,220,711 B1 | 4/2001 | Melville |
| 6,221,068 B1 | 4/2001 | Fried et al. |
| 6,229,139 B1 | 5/2001 | Neukermans et al. |
| 6,235,017 B1 | 5/2001 | Jegorov et al. |
| 6,243,186 B1 | 6/2001 | Melville |
| 6,245,590 B1 | 6/2001 | Wine et al. |
| 6,256,131 B1 | 7/2001 | Wine et al. |
| 6,257,727 B1 | 7/2001 | Melville |
| 6,272,907 B1 | 8/2001 | Neukermans et al. |
| 6,276,798 B1 | 8/2001 | Gil et al. |
| 6,281,862 B1 | 8/2001 | Tidwell et al. |
| 6,284,185 B1 | 9/2001 | Tokuda et al. |
| 6,285,489 B1 | 9/2001 | Helsel et al. |
| 6,285,505 B1 | 9/2001 | Melville et al. |
| 6,288,816 B1 | 9/2001 | Melville et al. |
| 6,292,287 B1 | 9/2001 | Fujinoki |
| 6,293,911 B1 | 9/2001 | Imaizumi et al. |
| 6,294,239 B1 | 9/2001 | Tokuda et al. |
| 6,294,775 B1 | 9/2001 | Seibel et al. |
| 6,317,103 B1 | 11/2001 | Furness, III et al. |
| 6,323,037 B1 | 11/2001 | Lauto et al. |
| 6,324,007 B1 | 11/2001 | Melville |
| 6,327,493 B1 | 12/2001 | Ozawa et al. |
| 6,331,909 B1 | 12/2001 | Dunfield |
| 6,333,110 B1 | 12/2001 | Barbera-Guillem |
| 6,338,641 B2 | 1/2002 | Nicholls |
| 6,352,344 B2 | 3/2002 | Tidwell |
| 6,353,183 B1 | 3/2002 | Ott et al. |
| 6,362,912 B1 | 3/2002 | Lewis et al. |
| 6,364,829 B1 | 4/2002 | Fulghum |

| Patent Number | Date | Inventor(s) |
|---|---|---|
| 6,369,928 B1 | 4/2002 | Mandella et al. |
| 6,369,953 B2 | 4/2002 | Melville et al. |
| 6,369,954 B1 | 4/2002 | Berge et al. |
| 6,370,406 B1 | 4/2002 | Wach et al. |
| 6,370,422 B1 | 4/2002 | Richards-Kortum et al. |
| 6,373,995 B1 | 4/2002 | Moore |
| 6,384,406 B1 | 5/2002 | Wine et al. |
| 6,388,641 B2 | 5/2002 | Tidwell et al. |
| 6,392,220 B1 | 5/2002 | Slater et al. |
| 6,396,461 B1 | 5/2002 | Lewis et al. |
| 6,414,779 B1 | 7/2002 | Mandella et al. |
| 6,417,502 B1 | 7/2002 | Stoner et al. |
| 6,423,956 B1 | 7/2002 | Mandella et al. |
| 6,425,900 B1 | 7/2002 | Knodel et al. |
| 6,426,013 B1 | 7/2002 | Neukermans et al. |
| 6,433,907 B1 | 8/2002 | Lippert et al. |
| 6,435,637 B1 | 8/2002 | Lyman |
| 6,441,356 B1 | 8/2002 | Mandella et al. |
| 6,445,362 B1 | 9/2002 | Tegreene |
| 6,447,524 B1 | 9/2002 | Knodel et al. |
| 6,462,770 B1 | 10/2002 | Cline et al. |
| 6,464,363 B1 | 10/2002 | Nishioka et al. |
| 6,467,345 B1 | 10/2002 | Neukermans et al. |
| 6,470,124 B1 | 10/2002 | Le Gargasson et al. |
| 6,477,403 B1 | 11/2002 | Eguchi et al. |
| 6,478,809 B1 | 11/2002 | Brotz |
| 6,485,413 B1 | 11/2002 | Boppart et al. |
| 6,492,962 B2 | 12/2002 | Melville et al. |
| 6,494,578 B1 | 12/2002 | Plummer et al. |
| 6,503,196 B1 | 1/2003 | Kehr et al. |
| 6,510,338 B1 | 1/2003 | Irion et al. |
| 6,512,622 B2 | 1/2003 | Wine et al. |
| 6,513,939 B1 | 2/2003 | Fettig et al. |
| 6,515,278 B2 | 2/2003 | Wine et al. |
| 6,515,781 B2 | 2/2003 | Lewis et al. |
| 6,520,972 B2 | 2/2003 | Peters |
| 6,522,444 B2 | 2/2003 | Mandella et al. |
| 6,525,310 B2 | 2/2003 | Dunfield |
| 6,527,708 B1 | 3/2003 | Nakamura et al. |
| 6,529,770 B1 | 3/2003 | Grimblatov |
| 6,530,698 B1 | 3/2003 | Kuhara et al. |
| 6,535,183 B2 | 3/2003 | Melville et al. |
| 6,535,325 B2 | 3/2003 | Helsel et al. |
| 6,537,211 B1 | 3/2003 | Wang et al. |
| 6,538,625 B2 | 3/2003 | Tidwell et al. |
| 6,545,260 B1 | 4/2003 | Katashiro et al. |
| 6,560,028 B2 | 5/2003 | Melville et al. |
| 6,563,105 B2 | 5/2003 | Seibel et al. |
| 6,563,106 B1 | 5/2003 | Bowers et al. |
| 6,572,606 B2 * | 6/2003 | Kliewer et al. .................. 606/5 |
| 6,583,117 B2 | 6/2003 | Owen et al. |
| 6,583,772 B1 | 6/2003 | Lewis et al. |
| 6,585,642 B2 | 7/2003 | Christopher |
| 6,603,552 B1 | 8/2003 | Cline et al. |
| 6,608,297 B2 | 8/2003 | Neukermans et al. |
| 6,639,570 B2 | 10/2003 | Furness, III et al. |
| 6,639,719 B2 | 10/2003 | Tegreene et al. |
| 6,650,877 B1 | 11/2003 | Tarbouriech et al. |
| 6,653,621 B2 | 11/2003 | Wine et al. |
| 6,654,158 B2 | 11/2003 | Helsel et al. |
| 6,661,393 B2 | 12/2003 | Tegreene et al. |
| 6,674,993 B1 | 1/2004 | Tarbouriech |
| 6,685,804 B1 | 2/2004 | Ikeda et al. |
| 6,687,034 B2 | 2/2004 | Wine et al. |
| 6,689,056 B1 | 2/2004 | Kilcoyne et al. |
| 6,699,170 B1 | 3/2004 | Crocker et al. |
| 6,700,552 B2 | 3/2004 | Kollin et al. |
| 6,714,331 B2 | 3/2004 | Lewis et al. |
| 6,734,835 B2 | 5/2004 | Tidwell et al. |
| 6,736,511 B2 | 5/2004 | Plummer et al. |
| 6,741,884 B1 | 5/2004 | Freeman et al. |
| 6,749,346 B1 | 6/2004 | Dickensheets et al. |
| 6,755,536 B2 | 6/2004 | Tegreene et al. |
| 6,762,867 B2 | 7/2004 | Lippert et al. |
| 6,768,588 B2 | 7/2004 | Urey |
| 6,771,001 B2 | 8/2004 | Mao et al. |
| 6,782,748 B2 | 8/2004 | Weber et al. |
| 6,786,382 B1 | 9/2004 | Hoffman |
| 6,795,221 B1 | 9/2004 | Urey |
| 6,802,809 B2 | 10/2004 | Okada |
| 6,803,561 B2 | 10/2004 | Dunfield |
| 6,821,245 B2 | 11/2004 | Cline et al. |
| 6,845,190 B1 | 1/2005 | Smithwick et al. |
| 6,856,436 B2 | 2/2005 | Brukilacchio et al. |
| 6,856,712 B2 | 2/2005 | Fauver et al. |
| 6,879,428 B2 | 4/2005 | Massieu |
| 6,888,552 B2 | 5/2005 | Debevec et al. |
| 6,894,823 B2 | 5/2005 | Taylor et al. |
| 6,899,675 B2 | 5/2005 | Cline et al. |
| 6,902,527 B1 | 6/2005 | Doguchi et al. |
| 6,905,057 B2 | 6/2005 | Swayze et al. |
| 6,939,364 B1 | 9/2005 | Soltz et al. |
| 6,957,898 B2 | 10/2005 | Yu |
| 6,967,757 B1 | 11/2005 | Allen et al. |
| 6,974,472 B2 | 12/2005 | Hong et al. |
| 6,975,898 B2 | 12/2005 | Seibel |
| 6,976,994 B2 | 12/2005 | Ballou et al. |
| 6,978,921 B2 | 12/2005 | Shelton, IV et al. |
| 6,985,271 B2 | 1/2006 | Yazdi et al. |
| 6,991,602 B2 | 1/2006 | Nakazawa et al. |
| 7,005,195 B2 | 2/2006 | Cheng et al. |
| 7,009,634 B2 | 3/2006 | Iddan et al. |
| 7,013,730 B2 | 3/2006 | Malametz |
| 7,015,956 B2 | 3/2006 | Luo et al. |
| 7,018,401 B1 | 3/2006 | Hyodoh et al. |
| 7,023,402 B2 | 4/2006 | Lewis et al. |
| 7,025,777 B2 | 4/2006 | Moore |
| 7,033,348 B2 | 4/2006 | Alfano et al. |
| 7,035,777 B2 | 4/2006 | Araki et al. |
| 7,061,450 B2 | 6/2006 | Bright et al. |
| 7,065,301 B2 | 6/2006 | Shastri et al. |
| 7,066,879 B2 | 6/2006 | Fowler et al. |
| 7,071,594 B1 | 7/2006 | Yan et al. |
| 7,071,931 B2 | 7/2006 | Tegreene et al. |
| 7,078,378 B1 | 7/2006 | Owen et al. |
| 7,108,656 B2 | 9/2006 | Fujikawa et al. |
| 7,112,302 B2 | 9/2006 | Yoshimi et al. |
| 7,126,903 B2 | 10/2006 | Feenstra et al. |
| 7,189,961 B2 | 3/2007 | Johnston et al. |
| 7,190,329 B2 | 3/2007 | Lewis et al. |
| 7,232,071 B2 | 6/2007 | Lewis et al. |
| 7,271,383 B2 | 9/2007 | Chee |
| 7,391,013 B2 | 6/2008 | Johnston et al. |
| 2001/0055462 A1 | 12/2001 | Seibel |
| 2002/0015724 A1 | 2/2002 | Yang et al. |
| 2002/0024495 A1 | 2/2002 | Lippert et al. |
| 2002/0050956 A1 | 5/2002 | Gerhard et al. |
| 2002/0075284 A1 | 6/2002 | Rabb, III |
| 2002/0088925 A1 | 7/2002 | Nestorovic et al. |
| 2002/0115922 A1 | 8/2002 | Waner et al. |
| 2002/0141026 A1 | 10/2002 | Wiklof et al. |
| 2002/0158814 A1 | 10/2002 | Bright et al. |
| 2002/0163484 A1 | 11/2002 | Furness, III et al. |
| 2002/0167462 A1 | 11/2002 | Lewis et al. |
| 2002/0171776 A1 | 11/2002 | Tegreene et al. |
| 2002/0171937 A1 | 11/2002 | Tegreene et al. |
| 2003/0016187 A1 | 1/2003 | Melville et al. |
| 2003/0030753 A1 | 2/2003 | Kondo et al. |
| 2003/0032143 A1 | 2/2003 | Neff et al. |
| 2003/0034709 A1 | 2/2003 | Jerman |
| 2003/0045916 A1 * | 3/2003 | Anderson et al. ............. 607/89 |
| 2003/0058190 A1 | 3/2003 | Lewis et al. |
| 2003/0086172 A1 | 5/2003 | Urey |
| 2003/0092995 A1 | 5/2003 | Thompson |
| 2003/0130562 A1 | 7/2003 | Barbato et al. |
| 2003/0142934 A1 | 7/2003 | Pan et al. |

| | | |
|---|---|---|
| 2003/0159447 A1 | 8/2003 | Sergio et al. |
| 2003/0214460 A1 | 11/2003 | Kovacs |
| 2003/0216729 A1 | 11/2003 | Marchitto et al. |
| 2004/0004585 A1 | 1/2004 | Brown et al. |
| 2004/0057103 A1 | 3/2004 | Bernstein |
| 2004/0075624 A1 | 4/2004 | Tegreene et al. |
| 2004/0076390 A1 | 4/2004 | Dong Yang et al. |
| 2004/0085261 A1 | 5/2004 | Lewis et al. |
| 2004/0085617 A1 | 5/2004 | Helsel et al. |
| 2004/0087844 A1 | 5/2004 | Yen |
| 2004/0101822 A1 | 5/2004 | Wiesner et al. |
| 2004/0113059 A1 | 6/2004 | Kawano et al. |
| 2004/0118821 A1 | 6/2004 | Han et al. |
| 2004/0119004 A1 | 6/2004 | Wine et al. |
| 2004/0122328 A1 | 6/2004 | Wang et al. |
| 2004/0133786 A1 | 7/2004 | Tarbouriech |
| 2004/0151466 A1 | 8/2004 | Crossman-Bosworth et al. |
| 2004/0155186 A1 | 8/2004 | Nestorovic et al. |
| 2004/0155834 A1 | 8/2004 | Wit et al. |
| 2004/0179254 A1 | 9/2004 | Lewis et al. |
| 2004/0196518 A1 | 10/2004 | Wine et al. |
| 2004/0223202 A1 | 11/2004 | Lippert et al. |
| 2004/0225222 A1 | 11/2004 | Zeng et al. |
| 2004/0236371 A1 | 11/2004 | McNally-Heintzelman et al. |
| 2004/0240866 A1 | 12/2004 | Ramsbottom |
| 2004/0252377 A1 | 12/2004 | Urey |
| 2004/0254474 A1 | 12/2004 | Seibel et al. |
| 2005/0010787 A1 | 1/2005 | Tarbouriech |
| 2005/0014995 A1 | 1/2005 | Amundson et al. |
| 2005/0020877 A1 | 1/2005 | Ishihara et al. |
| 2005/0020926 A1 | 1/2005 | Wiklof et al. |
| 2005/0023356 A1 | 2/2005 | Wiklof et al. |
| 2005/0030305 A1 | 2/2005 | Brown et al. |
| 2005/0038322 A1 | 2/2005 | Banik |
| 2005/0116038 A1 | 6/2005 | Lewis et al. |
| 2005/0162762 A1 | 7/2005 | Novak |
| 2005/0187441 A1 | 8/2005 | Kawasaki et al. |
| 2005/0203343 A1 | 9/2005 | Kang et al. |
| 2005/0240147 A1 | 10/2005 | Makower et al. |
| 2006/0010985 A1 | 1/2006 | Schneider |
| 2006/0084867 A1 | 4/2006 | Tremblay et al. |
| 2006/0164330 A1 | 7/2006 | Bright et al. |
| 2006/0183246 A1 | 8/2006 | Wiesner et al. |
| 2006/0195014 A1 | 8/2006 | Seibel et al. |
| 2006/0238774 A1 | 10/2006 | Lindner et al. |
| 2006/0245971 A1 | 11/2006 | Burns et al. |
| 2006/0284790 A1 | 12/2006 | Tegreene et al. |
| 2007/0027391 A1* | 2/2007 | Kohno ............ 600/427 |
| 2007/0038119 A1 | 2/2007 | Chen et al. |
| 2007/0046778 A1 | 3/2007 | Ishihara et al. |
| 2007/0135770 A1 | 6/2007 | Hunt et al. |
| 2007/0156021 A1 | 7/2007 | Morse et al. |
| 2007/0161876 A1 | 7/2007 | Bambot et al. |
| 2007/0162093 A1 | 7/2007 | Porter et al. |
| 2007/0167681 A1 | 7/2007 | Gill et al. |
| 2007/0173707 A1 | 7/2007 | Mitra |
| 2007/0179366 A1 | 8/2007 | Pewzner et al. |
| 2007/0197874 A1 | 8/2007 | Ishihara |
| 2007/0197875 A1 | 8/2007 | Osaka |
| 2007/0203413 A1 | 8/2007 | Frangioni |
| 2007/0213588 A1 | 9/2007 | Morishita et al. |
| 2007/0213618 A1 | 9/2007 | Li et al. |
| 2007/0225695 A1 | 9/2007 | Mayer et al. |
| 2007/0238930 A1 | 10/2007 | Wiklof et al. |
| 2007/0244365 A1 | 10/2007 | Wiklof |
| 2007/0260121 A1 | 11/2007 | Bakos et al. |
| 2007/0260273 A1 | 11/2007 | Cropper et al. |
| 2008/0058629 A1 | 3/2008 | Seibel et al. |
| 2008/0242967 A1* | 10/2008 | Weir ............ 600/407 |

FOREIGN PATENT DOCUMENTS

| | | |
|---|---|---|
| EP | 1139141 | 10/2001 |
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | WO 98/13720 | 4/1998 |
| WO | WO 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | WO 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

Kiang, M-H et al., "Surface-Micromachined Electrostatic-Comb Driven Scanning Micromirrors for Barcode Scanners" (date of first publication unknown).

Lewis, J.R. et al., "Scanned beam medical imager," MOEMS Display and Imaging Systems II, Proceedings of SPIE vol. 5348, pp. 40-51 (2004).

James, R. et al., "Update on MEMS-based Scanned Beam Imager" (date of first publication unknown).

Wiklof, C., "Display technology spawns laser camera," Laser Focus World (Dec. 2004).

"Press Information—Phillips' Fluid Lenses Bring Things into Focus," http://www.newscenter.philips.com (Mar. 3, 2004).

Lettice, J., "The $5 'no moving parts' fluid zoom lens—twice," The Register (Mar. 15, 2004).

"Volcano Products—IVUS Imaging Visions® PV018," http://www.volcanotherapeutics.com (date of first publication unknown).

Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).

"Crystalplex Technology—PlxBead™ Superior Qualities," http:www.crystalplex.com (date of first publication unknown).

"Microvision [illuminating information] Products/Overview, Corporate Overview Presentation 2006" (2006).

"Holographic Beam Combiner for Ladar, Printer, Fiber Optics, and Cancer Treatment," by Digital Optics Technologies, Inc., http://www.mdatechnology.net (date of first publication unknown).

Brown, D.M., Abstract from SPIE Digital Library for "High-power laser diode beam combiner," Optical Engineering, vol. 42, Issue 11 (2003).

Literature entitled "All fiber beam combiner from Point Source" (Oct. 13, 2006).

"Custom Polarzing Cube Beamsplitters," from GlobalSpec The Engineering Search Engine, http://www.globalspec.com (date of first publication unknown).

Literature entitled "Dallas Semiconductor MAXIM—Visible-Laser Driver has Digitally Controlled Power Modulation," by Maxim Integrated Products, http://www.maxim-ic.com (Jul. 1, 2001).

"SCAN Mode Strategies for SCUBA-2" (May 25, 2005).

Seifert, M. et al., "High Power Diode Laser Beam Scanning in Multi-Kilowatt Range," Proceedings of the 23rd International Congress on Applications of Lasers and Electro-Optics (2004).

Jutzi, B. et al., "Sub-Pixel Edge Localization Based on Laser Waveform Analysis," ISPRS WG III/3, III/4, V/3 Workshop "Laser scanning 2005," Enschede, the Netherlands (Sep. 12-14, 2005).

"Bladeless Trocars," by Johnson & Johnson, http://www.jnjgateway.com (date of first publication unknown).

Yeh, R. et al., "Microelectromechanical Components for Articulated Microrobots" (date of first publication unknown).

Xu, Q. et al., "Micrometre-scale silicon electro-optic modulator," Nature, vol. 435, pp. 325-327 (May 19, 2005).

Park, H. et al., "Development of Double-Sided Silicon Strip Position Sensor," 2005 IEEE Nuclear Science Symposium Conference Record, pp. 781-785 (2005).

Hammond, S.W., "Architecture and Operation of a Systolic Sparse Matrix Engine," Proceedings of the 3rd SIAM Conference on Parallel Processing for Scientific Computing, pp. 419-423 (1987).

International Search Report issued regarding International Application No. PCT/US2007/078868 (Mar. 28, 2008).

PCT, International Search Report, PCT/US2008/056589 (Jul. 30, 2008).

PCT, International Search Report, PCT/US2008/059231 (Jul. 4, 2008).

PCT, International Search Report, PCT/US2007/087923 (May 21, 2008).

PCT, International Search Report, PCT/US2008/056596 (Jun. 23, 2008).

PCT, International Search Report, PCT/US2008/059235 (Jul. 14, 2008).

PCT, International Search Report, PCT/US2007/087930 (Jul. 3, 2008).

PCT, International Search Report, PCT/US2008/051274 (Jul. 18, 2008).

PCT, International Search Report, PCT/US2008/066552 (Oct. 23, 2008).

Invitation to Pay Additional Fees with Partial International Search Report, PCT/US2008/074275 (Jan. 16, 2009).

Invitation to Pay Additional Fees with Partial International Search Report, PCT/US2008/074273 (Dec. 30, 2008).

* cited by examiner

APPARATUS AND METHOD FOR MEDICALLY TREATING A TATTOO

FIELD OF THE INVENTION

The present invention is related generally to tattoos, and more particularly to an apparatus and to a method for medically treating a tattoo.

BACKGROUND OF THE INVENTION

Conventional techniques for tattoo removal include a clinician directing a fixed-wavelength laser at the tattoo, wherein the laser heats the ink in the tattoo. The heat causes the ink to expand and break up into smaller particles. The body is able to then absorb the small ink fragments and carry them away. The number of sessions depends on the color of the ink of the tattoo. It is also known for a clinician to visually identify a first family of ink colors in the tattoo and use a first laser having a fixed wavelength suitable to remove the first family of ink colors of the tattoo, then to visually identify a different second family of ink colors in the tattoo and use a second laser having a fixed wavelength suitable to remove the different second family of ink colors of the tattoo, and then to visually identify a third family of ink colors in the tattoo and use a third laser having a fixed wavelength suitable to remove the different third family of ink colors of the tattoo.

What is needed is an improved apparatus and an improved method for medically treating a tattoo.

SUMMARY

A first expression of an embodiment of the invention is for apparatus for medically treating a tattoo of a patient. The apparatus includes a scanned light beam unit. The scanned light beam unit includes a light beam source assembly, a scanner, at least one light detector, and a controller. The light beam source assembly is adapted to emit light pulses at different wavelengths. The controller is operatively connected to the light beam source assembly and the scanner. The controller is adapted: to control the scanned light beam unit to illuminate a first light-pulse-sized region of the tattoo using the light beam source assembly at different wavelengths and at relatively low power; to use the at-least-one light detector to detect a least-reflecting wavelength of the illumination of the first light-pulse-sized region of the tattoo; and to control the scanned light beam unit to medically treat the first light-pulse-sized region of the tattoo using the light beam source assembly at a wavelength substantially equal to the least-reflecting wavelength of the illumination of the first light-pulse-sized region of the tattoo and at relatively high power to at least reduce the pigmentation of the first light-pulse-sized region of the tattoo.

A method of the invention is for medically treating a tattoo of a patient. The method includes obtaining a scanned light beam unit, wherein the scanned light beam unit includes a light beam source assembly, a scanner, at least one light detector, and a controller, wherein the light beam source assembly is adapted to emit light pulses at different wavelengths, and wherein the controller is operatively connected to the light beam source assembly and the scanner. The method includes having the controller control the scanned light beam unit to illuminate a first light-pulse-sized region of the tattoo using the light beam source assembly at different wavelengths and at relatively low power. The method includes having the controller use the at-least-one light detector to detect a least-reflecting wavelength of the illumination of the first light-pulse-sized region of the tattoo. The method includes having the controller control the scanned light beam unit to medically treat the first light-pulse-sized region of the tattoo using the light beam source assembly at a wavelength substantially equal to the least-reflecting wavelength of the illumination of the first light-pulse-sized region of the tattoo and at relatively high power to at least reduce the pigmentation of the first light-pulse-sized region of the tattoo.

A second expression of an embodiment of the invention is substantially identical to the first expression of the embodiment of the invention wherein, in the second expression, the scanned light beam unit is a medical-imaging-and-treatment scanned laser beam unit.

Several benefits and advantages are obtained from one or more of the expressions of an embodiment and the method of the invention. In one example, the least-reflecting wavelength for each light-pulse-sized region of colored ink in the tattoo determines the optimal wavelength ("color") to be used by the light (e.g., laser) beam source assembly to medically treat each light-pulse-sized region of colored ink in the tattoo. In one variation, an initial calibration is performed on an un-tattooed area of skin and later is used to identify un-tattooed light-pulse-sized regions not to be treated. In this example, there is no light energy deposition (and hence no ineffective treatment) in any neighboring light-pulse-sized region of un-tattooed skin or in any neighboring light-pulse-sized region of tattooed skin of the "wrong" color. In this example, the tattoo is medically treated on a light-pulse-sized region by light-pulse-sized region basis with each light-pulse-sized region, within the field of view of the scanned light beam unit, receiving light treatment with the corresponding optimal wavelength for that light-pulse-sized region.

DETAILED DESCRIPTION

Before explaining the several expressions of an embodiment and a method of the present invention in detail, it should be noted that each is not limited in its application or use to the details of construction and arrangement of parts and steps illustrated in the accompanying drawings and description. The illustrative expressions of the embodiment and the method of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiment and method of the present invention for the convenience of the reader and are not for the purpose of limiting the invention.

It is further understood that any one or more of the following-described expressions of an embodiment, examples, etc. can be combined with any one or more of the other following-described expressions of an embodiment, examples, etc.

Figure 1:
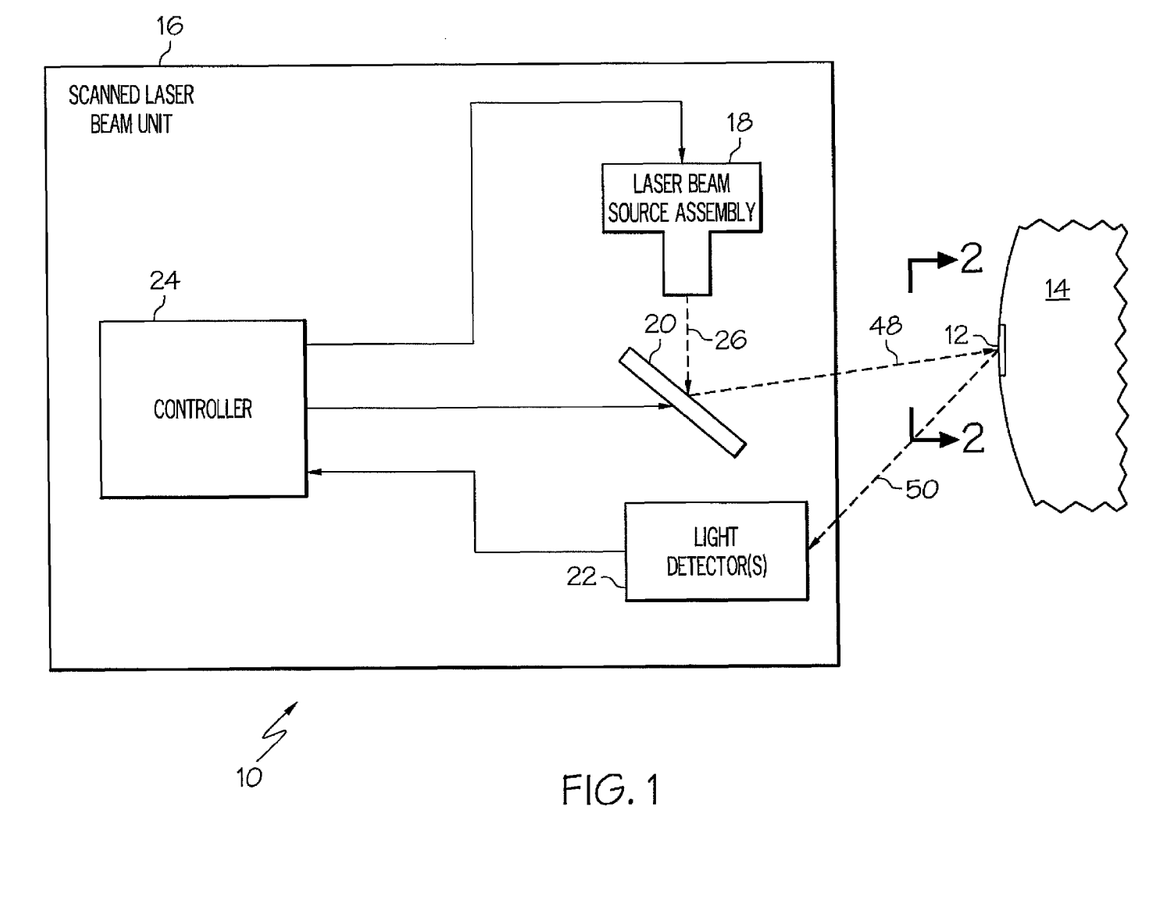
FIG. 1 is a schematic diagram of an embodiment of the invention including a scanned light (e.g., laser) beam unit having a light (e.g., laser) beam source assembly, a scanner, at least one light detector, and a controller and including a side view of a portion of a patient with a tattoo.
Figure 2:
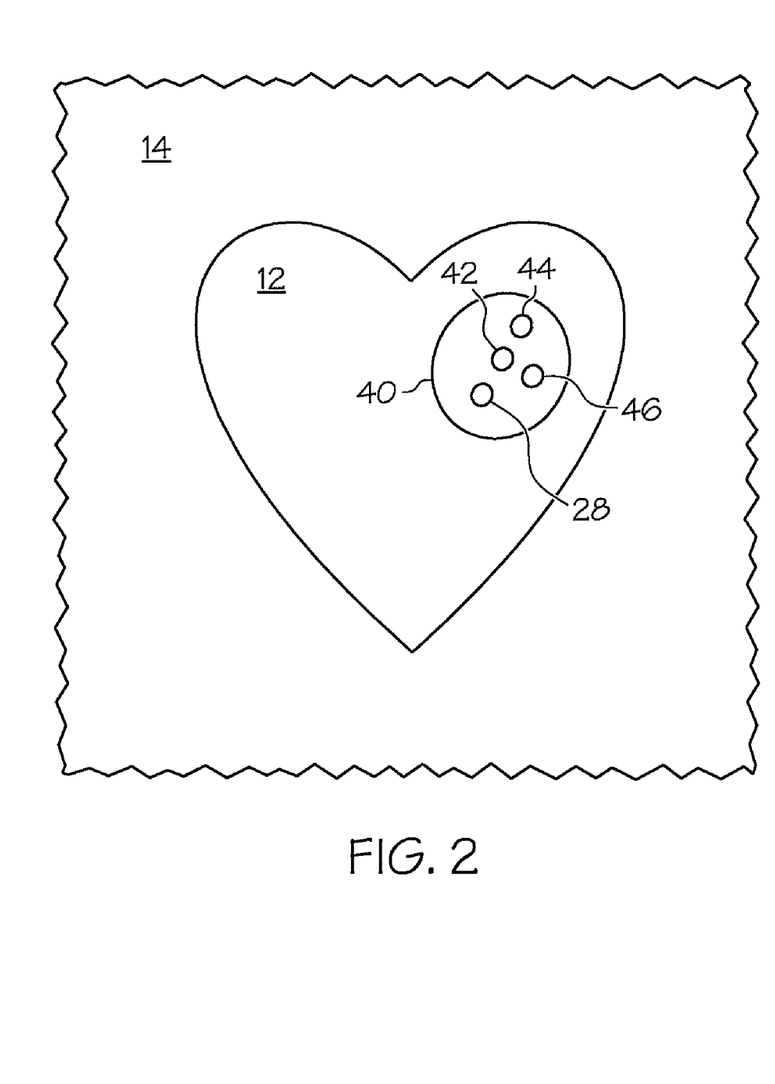
FIG. 2 is an enlarged view taken along lines 2-2 of FIG. 1 showing an area of skin of the patient which includes the tattoo.
Figure 3:
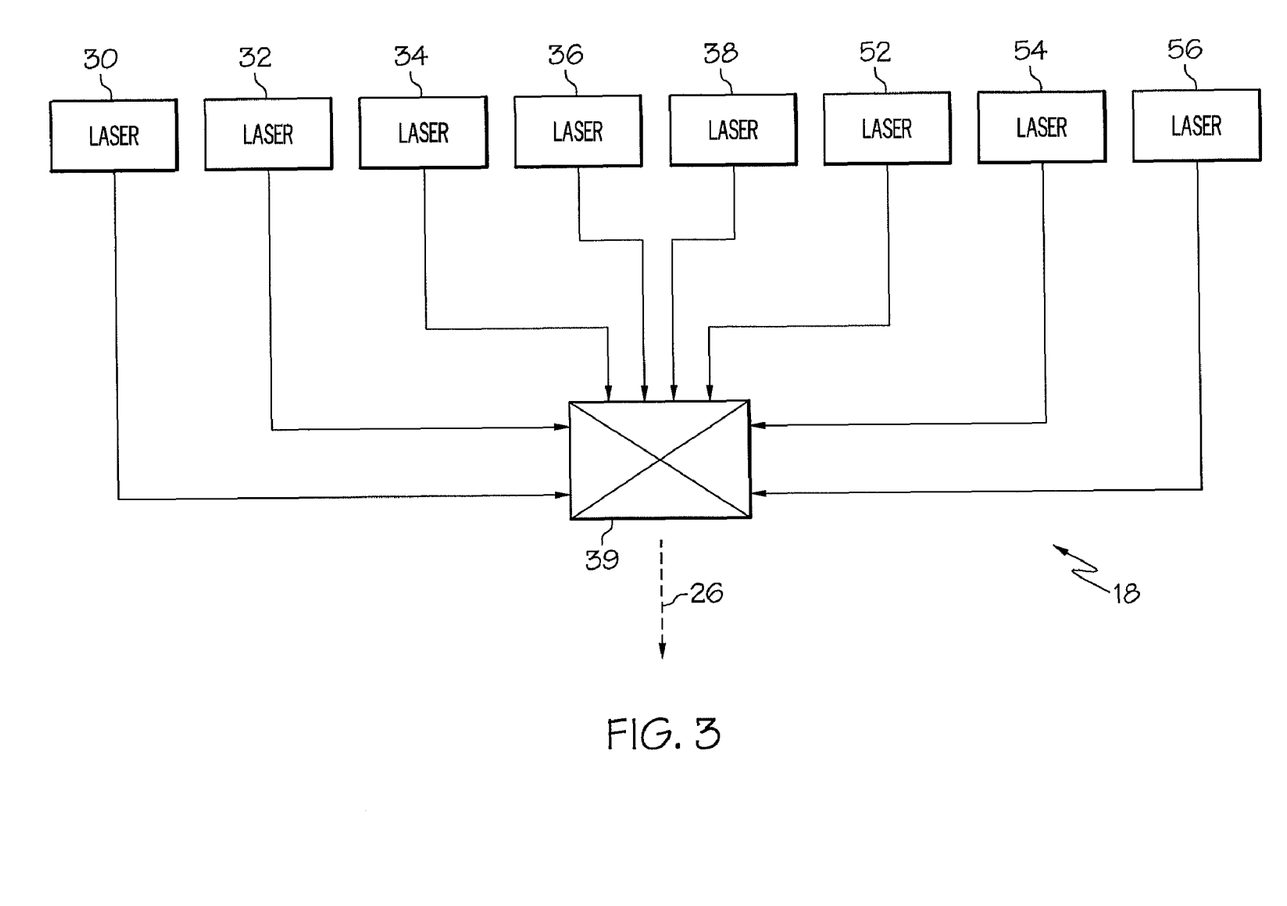
FIG. 3 is a schematic diagram of an embodiment of the light (e.g., laser) beam source assembly of the scanned light (e.g., laser) beam unit of FIG. 1.

An embodiment of the invention is shown in FIGS. 1-3. A first expression of the embodiment of FIGS. 1-3 is for apparatus 10 for medically treating a tattoo 12 of a patient 14 and includes a scanned light beam unit 16. The scanned light beam unit 16 includes a light beam source assembly 18, a scanner 20, at least one light detector 22, and a controller 24. The light beam source assembly 18 is adapted to emit light pulses 26 (indicated by a dashed line having a directional arrowhead in FIG. 1) at different wavelengths. The controller 24 is operatively connected to the light beam source assembly 18 and the scanner 20. The controller 24 is adapted: to control the scanned light beam unit 16 to illuminate a first light-pulse-sized region 28 (indicated best by one of the small circles in FIG. 2, wherein a non-circular light-pulse-sized region is left to the artisan) of the tattoo 12 using the light beam source assembly 18 at different wavelengths and at relatively low power; to use the at-least-one light detector 22 to detect a least-reflecting wavelength of the illumination of the first light-pulse-sized region 28 of the tattoo 12; and to control the scanned light beam unit 16 to medically treat the first light-pulse-sized region 28 of the tattoo 12 using the light beam source assembly 18 at a wavelength substantially equal to the least-reflecting wavelength and at relatively high power to at least reduce the pigmentation of the first light-pulse-sized region 28 of the tattoo 12.

It is noted that a tattoo is ink and/or dye embedded in the dermis. It is also noted that "reducing the pigmentation" means reducing the concentration of such embedded ink and/or dye. It is further noted that the unlabeled solid lines having directional arrowheads in FIG. 1 represent signals to and from the controller 24.

An example of an endoscope application of a medical-imaging scanned laser beam unit is given in US Patent Application Publication 2005/0020926 wherein a two-dimensional MEMS (micro-electromechanical system) scanner is disclosed which scans one or more light beams (such as light beams from red, green and blue lasers) at high speed in a pattern that covers an entire two-dimensional field of view or a selected region of a two-dimensional field of view and which uses at least one light detector in creating an image from the reflected light for display on a monitor.

In one enablement of the first expression of the embodiment of FIGS. 1-3, the scanned light beam unit 16 has a fixed prime focus spatial resolution, and the first light-pulse-sized region 28 has substantially a same size and shape as the fixed prime focus spatial resolution. In one illustration, the fixed prime focus spatial resolution has a substantially circular shape with a diameter between and including 0.005 millimeters and 0.5 millimeters. Non-circular illustrations are left to the artisan. In one configuration, the scanned light beam unit 16 is housed in a handpiece whose distal end is in contact with the tattoo 12. Other configurations, including robotic applications, are left to the artisan.

In one application of the first expression of the embodiment of FIGS. 1-3, the light beam source assembly 18 includes at least one light beam source 30 and 32 having a tunable wavelength. In one variation, the light beam source assembly 18 includes a plurality of light beam sources 30 and 32 each having a tunable wavelength. In a different variation, the light beam source assembly has only one light beam source wherein the light beam source has a tunable wavelength and wherein the light beam source has a relatively low power mode and a relatively high power mode. In the same or a different application, the light beam source assembly 18 includes a plurality of light beam sources 34, 36 and 38 each having a fixed wavelength. In one variation, the light beam source assembly 18 includes at least one light beam source 30 and 32 having a tunable wavelength. In a different variation, the light beam source assembly has only a plurality of light beam sources each having a fixed wavelength, each having a relatively low power mode, and each having a relatively high power mode. Other applications and variations are left to the artisan.

It is noted that the unlabeled solid lines having directional arrowheads in FIG. 3 represent light from the light beam sources 30-38 and 52-56 before such light leaves the light beam source assembly 18. In one example, the light beam source assembly 18 includes a combiner 39 controlled by the controller 24 and adapted to either pass light from only one of the light beam sources 30-38 and 52-56 or to combine light from two or more light beam sources 30-38 and 52-56. In one illustration, the light beam source assembly 18 is a laser beam source assembly.

In one employment, the controller 24 tunes a tunable-wavelength laser beam source to a particular wavelength or chooses a laser beam source having a particular wavelength, wherein the particular wavelength is the closest of the available wavelengths of the light beam source assembly 18 to the least-reflecting wavelength, and wherein, for the purposes of describing the expressions of the embodiment and the method of the invention, such particular wavelength is said to be substantially equal to the least-reflecting wavelength. In one example, such particular wavelength is within ten percent of the least-reflecting wavelength.

In one implementation of the first expression of the embodiment of FIGS. 1-3, the scanned light beam unit 16 has a field of view 40 (indicated by a large circle in FIG. 2, wherein a non-circular field of view is left to the artisan). In one variation, the controller 24 is adapted: to control the scanned light beam unit 16 to illuminate each other light-pulse-sized region 42, 44 and 46 (only three of which are shown and are indicated by the other small circles of FIG. 2) of the tattoo 12 within the field of view 40 using the light beam source assembly 18 at different wavelengths and at relatively low power; and to use the at-least-one light detector 22 to detect a least-reflecting wavelength of the illumination of each other light-pulse-sized region 42, 44 and 46 of the tattoo 12 within the field of view 40. In one modification, the controller 24 is adapted to control the scanned light beam unit 16 to medically treat each other light-pulse-sized region 42, 44 and 46 of the tattoo 12 within the field of view 40 using the light beam source assembly 18 at a wavelength for each other light-pulse-sized region 42, 44 and 46 of the tattoo 12 within the field of view 40 substantially equal to the corresponding least-reflecting wavelength of the illumination of each other light-pulse-sized region 42, 44 and 46 of the tattoo 12 within the field of view 40 and at relatively high power to at least reduce the pigmentation of each other light-pulse-sized region 42, 44 and 46 of the tattoo 12 within the field of view 40.

A method of the invention is for medically treating a tattoo 12 of a patient 14 and includes steps a) through d).

Step a) includes obtaining a scanned light beam unit 16, wherein the scanned light beam unit 16 includes a light beam source assembly 18, a scanner 20, at least one light detector 22, and a controller 24, wherein the light beam source assembly 18 is adapted to emit light pulses 26 at different wavelengths, and wherein the controller 24 is operatively connected to the light beam source assembly 18 and the scanner 20.

Step b) includes having the controller 24 control the scanned light beam unit 16 to illuminate a first light-pulse-sized region 28 of the tattoo 12 using the light beam source assembly 18 at different wavelengths and at relatively low power. In one variation, the different wavelengths of light pulses 26 are emitted sequentially. In a different variation, the different wavelengths of light pulses 26 are emitted simultaneously. FIG. 1 shows the emitted light pulses 26 being reflected by the scanner 20 as scanned light 48 (indicated by a dashed line having a directional arrowhead in FIG. 1) onto the first light-pulse-sized region 28 (indicated in FIG. 1 by the un-labeled end of the arrowhead of dashed line 48 and in FIG. 2 by one of the small circles) which illuminates the first light-pulse-sized region 28 of the tattoo 12.

Step c) includes having the controller 24 use the at-least-one light detector 22 to detect a least-reflecting wavelength of the illumination of the first light-pulse-sized region 28 of the tattoo 12. FIG. 1 shows reflected light 50 (indicated by a dashed line having a directional arrowhead in FIG. 1) which is the scanned light 48 which has been reflected by the first light-pulse-sized region 28 of the tattoo 12 directly or indirectly to the at-least-one light detector 22. As used in the present application, "reflected light 50" means light which has been detected by the at-least-one light detector 22 whether from true reflection, scattering, and/or refraction, etc. In one variation, at least one optical fiber (not shown) receives the reflected light 50 and transmits it to the at-least-one light detector 22. Various techniques for detecting a least-reflecting wavelength are known to those skilled in the art including, without limitation, determining the wavelength having the minimum light intensity for the reflected light 50.

In one technique, the light beam source assembly 18 includes a plurality of medical-imaging light beam sources 52 (e.g., a red laser beam source), 54 (e.g., a green laser beam source) and 56 (e.g., a blue laser beam source) each having a fixed wavelength which image the first light-pulse-sized region 28 of the tattoo 12. In this technique, the controller 24 uses the at-least-one light detector 22 to determine, from the reflected light 50, the least-reflecting wavelength of the reflected light 50.

Step d) includes having the controller 24 control the scanned light beam unit 16 to medically treat the first light-pulse-sized region 28 of the tattoo 12 using the light beam source assembly 18 at a wavelength substantially equal to the least-reflecting wavelength of the illumination of the first light-pulse-sized region 28 of the tattoo 12 and at relatively high power to at least reduce the pigmentation of the first light-pulse-sized region 28 of the tattoo 12. In one variation, the same light beam source or sources(s) of the light beam source assembly 18 are used at relatively low power in step b) and are used at relatively high power in step d). In a different variation, step b) is performed using a relatively low power light beam source or sources of the light beam source assembly 18, and step d) is performed using a relatively high power and different light beam source of the light beam source assembly 18. In one employment, step d) uses a pulsed laser (an intrinsic pulsed laser or a continuous-wave laser with an electronic optical shutter).

In one extension of the method, wherein the scanned light beam unit 16 has a field of view 40, the method includes steps e) and f). Step e) includes having the controller 24 control the scanned light beam unit 16 to illuminate each other light-pulse-sized region 42, 44 and 46 of the tattoo 12 within the field of view 40 using the light beam source assembly 18 at different wavelengths and at relatively low power. Step f) includes having the controller 24 use the at-least-one light detector 22 to detect a least-reflecting wavelength of the illumination of each other light-pulse-sized region 42, 44 and 46 of the tattoo 12 within the field of view 40.

In the same extension of the method, the method includes step g). Step g) includes having the controller 24 control the scanned light beam unit 16 to medically treat each other light-pulse-sized region 42, 44 and 46 of the tattoo 12 within the field of view 40 using the light beam source assembly 18 at a wavelength for each other light-pulse-sized region 42, 44 and 46 of the tattoo 12 within the field of view 40 substantially equal to the corresponding least-reflecting wavelength of the illumination of each other light-pulse-sized region 42, 44 and 46 of the tattoo 12 within the field of view 40 and at relatively high power to at least reduce the pigmentation of each other light-pulse-sized region 42, 44 and 46 of the tattoo 12 within the field of view 40. In one variation, steps b) and e) are performed before steps c) and f), and steps c) and f) are performed before steps d) and g).

In one employment of the method, the light beam source assembly 18 includes a plurality of medical-imaging light beam sources 52, 54 and 56 used to image the field of view, the controller 24 uses the at-least-one light detector 22 to estimate the least-reflecting wavelength (or color) of each light-pulse-sized region 28, 42, 44 and 46 of the tattoo 12 in the field of view 40, and the controller 24 uses the estimated least-reflecting wavelength for a particular light-pulse-sized region in choosing a wavelength of a light beam source to use for the particular light-pulse-sized region in steps d) and g) of the method.

A second expression of the embodiment of FIGS. 1-3 is for apparatus 10 for medically treating a tattoo 12 of a patient 14 and is substantially identical to the first expression of the embodiment of FIGS. 1-3 in paragraph [0018] wherein, in the second expression, the scanned light beam unit 16 is a medical-imaging-and-treatment scanned laser beam unit.

In one example, the second expression of the embodiment of FIGS. 1-3 includes the implementation of the first expression of the embodiment of FIGS. 1-3 of paragraph [0025] with the addition that the controller 24 is adapted to create a map correlating the first light-pulse-sized region 28 of the tattoo 12 and each other light-pulse-sized region 42, 44 and 46 of the tattoo 12 within the field of view 40 with the corresponding least-reflecting wavelength and wherein medical treatment of each other light-pulse-sized region 42, 44 and 46 of the tattoo 12 within the field of view 40 is in accordance with the created map. In one variation, the treatment of the first light-pulse-sized region 28 is also in accordance with the created map.

In one application of the second expression of the embodiment of FIGS. 1-3, the laser beam source assembly 18 includes at least one laser beam source 30 and 32 having a tunable wavelength and which, in one example, is a medical-treatment at-least-one laser beam source. In one variation, the laser beam source assembly 18 includes at least one medical-imaging laser beam source 52, 54 and 56 having a fixed wavelength. In the same or a different application, the laser beam source assembly 18 includes a plurality of laser beam sources 34, 36 and 38 each having a fixed wavelength and, in one example, each being a medical-treatment laser beam source. In one variation, the laser beam source assembly 18 includes at least one medical-imaging laser beam source 52, 54 and 56 having a fixed wavelength. Other applications are left to the artisan. It is noted that a medical-imaging laser beam source includes a medical-imaging-only laser beam source and a medical-imaging-and-treatment laser beam source (e.g., image at low power and treat at high power), and that a medical-treatment laser beam source includes a medical-treatment-only laser beam source and a medical-imaging-and-treatment laser beam source.

In one enablement of the second expression of the embodiment of FIGS. 1-3, the scanned laser beam unit 16 has a fixed prime focus spatial resolution having a substantially circular shape with a diameter between and including 0.005 millimeters and 0.5 millimeters.

Several benefits and advantages are obtained from one or more of the expressions of an embodiment and the method of the invention. In one example, the least-reflecting wavelength for each light-pulse-sized region of colored ink in the tattoo determines the optimal wavelength ("color") to be used by the light (e.g., laser) beam source assembly to medically treat each light-pulse-sized region of colored ink in the tattoo. In one variation, an initial calibration is performed on an untattooed area of skin and later is used to identify un-tattooed light-pulse-sized regions not to be treated. In this example, there is no light energy deposition (and hence no ineffective treatment) in any neighboring light-pulse-sized region of untattooed skin or in any neighboring light-pulse-sized region of tattooed skin of the "wrong" color. In this example, the tattoo is medically treated on a light-pulse-sized region by light-pulse-sized region basis with each light-pulse-sized region, within the field of view of the scanned light beam unit, receiving light treatment with the corresponding optimal wavelength for that light-pulse-sized region.

While the present invention has been illustrated by a description of several expressions of an embodiment and a method, it is not the intention of the applicant to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. Apparatus for medically treating a tattoo of a patient comprising a scanned light beam unit, wherein the scanned light beam unit includes a light beam source assembly, a scanner, at least one light detector, and a controller, wherein the light beam source assembly is adapted to emit light pulses at different wavelengths, wherein the controller is operatively connected to the light beam source assembly and the scanner, and wherein the controller is adapted:
    to control the scanned light beam unit to illuminate a first light-pulse-sized region of the tattoo using the light beam source assembly at different wavelengths and at relatively low power;
    to use the at-least-one light detector to detect a least-reflecting wavelength of the illumination of the first light-pulse-sized region of the tattoo; and
    to control the scanned light beam unit to medically treat the first light-pulse-sized region of the tattoo using the light beam source assembly at a wavelength substantially equal to the detected least-reflecting wavelength of the illumination of the first light-pulse-sized region of the tattoo and at relatively high power to at least reduce the pigmentation of the first light-pulse-sized region of the tattoo.

2. The apparatus of claim 1, wherein the scanned light beam unit has a fixed prime focus spatial resolution, and wherein the illumination of the first light-pulse-sized region has substantially a same size and shape as the fixed prime focus spatial resolution.

3. The apparatus of claim 2, wherein the fixed prime focus spatial resolution has a substantially circular shape with a diameter between and including 0.005 millimeters and 0.5 millimeters.

4. The apparatus of claim 1, wherein the light beam source assembly includes at least one light beam source having a tunable wavelength.

5. The apparatus of claim 4, wherein the light beam source assembly includes a plurality of light beam sources each having a tunable wavelength.

6. The apparatus of claim 1, wherein the light beam source assembly includes a plurality of light beam sources each having a fixed wavelength.

7. The apparatus of claim 6, wherein the light beam source assembly includes at least one additional light beam source having a tunable wavelength.

8. The apparatus of claim 1, wherein the scanned light beam unit has a field of view encompassing a plurality of light-pulse-sized-regions, and wherein the controller is adapted:
    to control the scanned light beam unit to illuminate each other light-pulse-sized region of the tattoo within the field of view using the light beam source assembly at different wavelengths and at relatively low power; and
    to use the at-least-one light detector to detect a least-reflecting wavelength of the illumination of each other light-pulse-sized region of the tattoo within the field of view.

9. The apparatus of claim 8, wherein the controller is adapted to control the scanned light beam unit to medically treat each other light-pulse-sized region of the tattoo within the field of view using the light beam source assembly at a wavelength for each other light-pulse-sized region of the tattoo within the field of view substantially equal to the corresponding least-reflecting wavelength of the illumination of each other light-pulse-sized region of the tattoo within the field of view and at relatively high power to at least reduce the pigmentation of each other light-pulse-sized region of the tattoo within the field of view.

10. A method for medically treating a tattoo of a patient comprising the steps of:
    a) obtaining a scanned light beam unit, wherein the scanned light beam unit includes a light beam source assembly, a scanner, at least one light detector, and a controller, wherein the light beam source assembly is adapted to emit light pulses at different wavelengths, and wherein the controller is operatively connected to the light beam source assembly and the scanner;
    b) having the controller control the scanned light beam unit to illuminate a first light-pulse-sized region of the tattoo using the light beam source assembly at different wavelengths and at relatively low power;
    c) having the controller use the at-least-one light detector to detect a least-reflecting wavelength of the illumination of the first light-pulse-sized region of the tattoo; and
    d) having the controller control the scanned light beam unit to medically treat the first light-pulse-sized region of the tattoo using the light beam source assembly at a wavelength substantially equal to the detected least-reflecting wavelength of the illumination of the first light-pulse-sized region of the tattoo and at relatively high power to at least reduce the pigmentation of the first light-pulse-sized region of the tattoo.

11. The method of claim 10, wherein the scanned light beam unit has a field of view encompassing a plurality of light-pulse-sized-regions, and also including the steps of:
    e) having the controller control the scanned light beam unit to illuminate each other light-pulse-sized region of the tattoo within the field of view using the light beam source assembly at different wavelengths and at relatively low power; and f) having the controller use the at-least-one light detector to detect a least-reflecting wavelength of the illumination of each other light-pulse-sized region of the tattoo within the field of view.

12. The method of claim 11, also including the step of:
g) having the controller control the scanned light beam unit to medically treat each other light-pulse-sized region of the tattoo within the field of view using the light beam source assembly at a wavelength for each other light-pulse-sized region of the tattoo within the field of view substantially equal to the corresponding least-reflecting wavelength of the illumination of each other light-pulse-sized region of the tattoo within the field of view and at relatively high power to at least reduce the pigmentation of each other light-pulse-sized region of the tattoo within the field of view.

13. Apparatus for medically treating a tattoo of a patient comprising a scanned laser beam unit, wherein the scanned laser beam unit is a medical-imaging-and-treatment scanned laser beam unit, wherein the scanned laser beam unit includes a laser beam source assembly, a scanner, at least one light detector, and a controller, wherein the laser beam source assembly is adapted to emit laser light pulses at different wavelengths, wherein the controller is operatively connected to the laser beam source assembly and the scanner, and wherein the controller is adapted:
to control the scanned laser beam unit to illuminate a first light-pulse-sized region of the tattoo using the laser beam source assembly at different wavelengths and at relatively low power;
to use the at-least-one light detector to detect a least-reflecting wavelength of the illumination of the first light-pulse-sized region of the tattoo; and
to control the scanned laser beam unit to medically treat the first light-pulse-sized region of the tattoo using the laser beam source assembly at a wavelength substantially equal to the least-reflecting wavelength of the illumination of the first light-pulse-sized region of the tattoo and at relatively high power to at least reduce the pigmentation of the first light-pulse-sized region of the tattoo.

14. The apparatus of claim 13, wherein the scanned laser beam unit has a field of view encompassing a plurality of light-pulse-sized-regions, and wherein the controller is adapted:
to control the scanned laser beam unit to illuminate each other light-pulse-sized region of the tattoo within the field of view using the laser beam source assembly at different wavelengths and at relatively low power;
to use the at-least-one light detector to detect a least-reflecting wavelength of the illumination of each other light-pulse-sized region of the tattoo within the field of view; and
to create a map correlating the first light-pulse-sized region of the tattoo and each other light-pulse-sized region of the tattoo within the field of view with the corresponding least-reflecting wavelength.

15. The apparatus of claim 14, wherein the controller is adapted to control the scanned laser beam unit to medically treat each other light-pulse-sized region of the tattoo within the field of view according to the created map using the laser beam source assembly at a wavelength for each other light-pulse-sized region of the tattoo within the field of view substantially equal to the corresponding least-reflecting wavelength of the illumination of each other light-pulse-sized region of the tattoo within the field of view and at relatively high power to at least reduce the pigmentation of each other light-pulse-sized region of the tattoo within the field of view.

16. The apparatus of claim 15, wherein the laser beam source assembly includes at least one laser beam source which has a tunable wavelength and which is a medical-treatment at-least-one laser beam source.

17. The apparatus of claim 16, wherein the laser beam source assembly includes at least one laser beam source which has a fixed wavelength and which is a medical-imaging at-least-one laser beam source.

18. The apparatus of claim 13, wherein the laser beam source assembly includes a plurality of laser beam sources which each have a fixed wavelength and which each are a medical-treatment laser beam source.

19. The apparatus of claim 18, wherein the laser beam source assembly includes at least one laser beam source which has a fixed wavelength and which is a medical-imaging at-least-one laser beam source.

20. The apparatus of claim 13, wherein the scanned laser beam unit has a fixed prime focus spatial resolution having a substantially circular shape with a diameter between and including 0.005 millimeters and 0.5 millimeters.

* * * * *